US011950788B2

(12) United States Patent
Haberman et al.

(10) Patent No.: US 11,950,788 B2
(45) Date of Patent: Apr. 9, 2024

(54) GRAFT PLACEMENT SYSTEM

(71) Applicant: Smith & Nephew, Inc., Memphis, TN (US)

(72) Inventors: Daniel Haberman, Hoboken, NJ (US); Stephen A. Santangelo, Sturbridge, MA (US); Nikhil N. Verma, Chicago, IL (US)

(73) Assignee: SMITH & NEPHEW, INC., Memphis, TN (US)

( * ) Notice: Subject to any disclaimer, the term of this patent is extended or adjusted under 35 U.S.C. 154(b) by 1528 days.

(21) Appl. No.: 16/207,267

(22) Filed: Dec. 3, 2018

(65) Prior Publication Data

US 2019/0099190 A1 Apr. 4, 2019

Related U.S. Application Data

(62) Division of application No. 14/753,418, filed on Jun. 29, 2015, now Pat. No. 10,172,627.

(51) Int. Cl.
*A61B 17/17* (2006.01)
*A61B 17/16* (2006.01)
*A61B 17/88* (2006.01)
*A61B 90/00* (2016.01)
*A61B 17/28* (2006.01)
*A61F 2/28* (2006.01)

(52) U.S. Cl.
CPC .......... *A61B 17/1635* (2013.01); *A61B 17/17* (2013.01); *A61B 17/1739* (2013.01); *A61B 90/06* (2016.02); *A61B 17/1778* (2016.11); *A61B 2017/2808* (2013.01); *A61B 17/8866* (2013.01); *A61B 2090/061* (2016.02); *A61F 2002/2835* (2013.01); *A61F 2002/285* (2013.01)

(58) Field of Classification Search
CPC . A61B 17/1635; A61B 17/17; A61B 17/1739; A61B 17/1778; A61B 17/8866; A61B 2017/2808; A61B 2090/061; A61B 17/1782; A61B 90/06; A61F 2002/2835; A61F 2002/285
See application file for complete search history.

(56) References Cited

U.S. PATENT DOCUMENTS 2,181,746 A * 11/1939 Siebrandt ............. A61B 17/282
7/125
4,633,862 A * 1/1987 Petersen ............ A61B 17/2812
606/88

(Continued)

OTHER PUBLICATIONS

Chinese Application No. 201680038680.3 First Office Action dated Nov. 5, 2019.

(Continued)

*Primary Examiner* — Marcia L Watkins
(74) *Attorney, Agent, or Firm* — Burns & Levinson, LLP; Joseph M. Maraia; Marlo Schepper Grolnic (57) ABSTRACT

Embodiments of the invention include a system for coupling a graft to a bone. A graft preparation tool may be used to place one or more holes in a graft and an offset measurement tool may be used to determine the distance of the one or more holes from an edge of the graft to be aligned with a portion of the bone. One or more complementary holes may then be created in the bone and fasteners applied through the holes to couple the graft to the bone.

15 Claims, 8 Drawing Sheets

(56) References Cited

U.S. PATENT DOCUMENTS

| | | | | |
|---|---|---|---|---|
| 5,697,933 | A * | 12/1997 | Gundlapalli | A61F 2/0811 |
| | | | | 606/206 |
| 6,033,359 | A * | 3/2000 | Doi | A61B 5/1076 |
| | | | | 606/1 |
| 6,916,325 | B2 * | 7/2005 | Kana | A61F 2/4657 |
| | | | | 606/89 |
| 9,198,732 | B2 * | 12/2015 | Iannotti | A61B 17/1739 |
| 9,592,008 | B2 * | 3/2017 | Olivera | A61B 17/12104 |
| 10,806,472 | B2 * | 10/2020 | Bettenga | A61B 17/1778 |
| 2009/0318923 | A1 * | 12/2009 | Burkhart | A61F 2/30734 |
| | | | | 606/87 |
| 2013/0172898 | A1 * | 7/2013 | Iannotti | A61B 17/3403 |
| | | | | 606/102 |

OTHER PUBLICATIONS

Chinese Application No. 201680038680.3 Text of First Office Action.
Chinese Application No. 201680038680.3 Search Report.
Communication received for corresponding European patent application No. 16731769.2-1122 dated Apr. 6, 2020.

* cited by examiner

GRAFT PLACEMENT SYSTEM

CROSS-REFERENCE TO RELATED APPLICATIONS

This application is a division of U.S. patent application Ser. No. 14/753,418 filed on Jun. 29, 2015, all of the disclosure of which is incorporated herein by reference in its entirety.

FIELD OF THE INVENTION

The present invention relates generally to the field of placing grafts with surgical instruments, and more particularly relates to surgical instruments and methods used to align portions of a graft with a bone to which the graft is to be coupled. Some embodiments include use of a specially configured instrument to measure an offset from a hole in the graft to a portion of the graft to be aligned with the bone.

BACKGROUND

Some surgical grafting procedures require that a graft be attached to a bone in a very specific location. For example, where an edge or a face of a graft is to be aligned with an edge or a face of a bone to which the graft is to be coupled to provide a bearing surface across the graft and the bone, alignment must be precise. In such circumstances, a system and method for reliably and accurately placing the graft is needed. One example of such a situation is a Latarjet protocol procedure, which requires that one or more holes be drilled into a severed piece of a coracoid graft and a glenoid. The respective hole or holes must align such that placing one or more fasteners through the one or more holes will fix a lateral edge of the coracoid graft flush with an articular surface of the glenoid. The accurate placement of the one or more drill holes is critical to a successful alignment in a Latarjet protocol procedure and many other procedures.

It would be advantageous to provide surgical instruments that provide for controlled placement of one or more holes through a graft and that provide for accurate measurement of the one or more holes as placed relative to portions of a graft to be aligned with a bone to which the graft is to be coupled. The instrument or instruments for enabling controlled placement of the holes may be separate from the instrument or instruments for accurately measuring placement of the one or more holes. It may be further advantageous to provide a method that enable a surgeon to keep the graft separated from the bone to which the graft is to be coupled while one or more holes for fasteners are created in the bone so that a clear view of the tissue into which a hole is being created may be maintained during drilling. Some improved embodiments may include a collection or kit of multiple instruments and may also include implants. Such a collection or kit may promote efficient performance of graft alignment surgical procedures, such as but not limited to, Latarjet protocol procedures.

SUMMARY

An embodiment of the invention is a system for coupling a graft to a bone that may include a graft preparation tool, an offset measurement tool, and an offset drill guide. The graft preparation tool may include a holder in which a graft may be positioned, and a drilling alignment mechanism configured to guide placement of one or more holes in a graft. The offset measurement tool may include a body and a pin with a cross-sectional center axis. The pin may be coupled to the body and sized to fit within at least one of the one or more holes in the graft. The offset measurement tool may also include two or more legs coupled to the body and extending to two or more different distances from the cross-sectional center axis of the pin. The offset drill guide may include a drill positioning opening, and an alignment surface set a distance from the drill positioning opening. The distance set from the drill positioning opening is coordinated with the offset measured with the offset measurement tool.

Another embodiment of the invention is an offset measurement tool that includes a body and a pin with a cross-sectional center axis, the pin coupled to the body and sized to fit within at least one of one or more holes in a graft. Embodiments of the offset measurement tool may also include two or more legs coupled to the body and extending to two or more different distances from the cross-sectional center axis of the pin.

Yet another embodiment of the invention is a method of performing a Latarjet protocol procedure. The method may include severing at least a portion of coracoid process from a patient, drilling one or more holes in the severed coracoid process, and providing an offset measurement tool. The offset measurement tool may include a body and a pin with a cross-sectional center axis, the pin coupled to the body. The pin may be sized to fit within at least one of the one or more holes in the severed coracoid process. The offset measurement tool may also include two or more legs coupled to the body and extending to two or more different distances from the cross-sectional center axis of the pin. Method embodiments may also include measuring an offset distance from a first one of the holes in the severed coracoid process to an edge of the severed coracoid process that is to be aligned with a face of a glenoid of the patient by inserting the pin of the offset measurement tool into the first one of the holes in the severed coracoid process and observing which extent of one of the two or more legs most nearly aligns with the edge of the severed coracoid process that is to be aligned with a face of a glenoid, the observation occurring when the offset measurement tool is rotated about the axis of the first one of the holes in the severed coracoid process. Embodiments may additionally include selecting an offset drill guide that correlates with the offset distance measured from the first one of the holes in the severed coracoid process to an edge of the severed coracoid process with the offset measurement tool, aligning a portion of the offset drill guide with the face of the glenoid, and drilling a first hole in the glenoid through the offset drill guide. The first one of the holes in the severed coracoid process may then be aligned with the first hole in the glenoid, and some method embodiments include inserting a first screw through the first one of the holes in the severed coracoid process and through the first hole in the glenoid to couple the severed coracoid process to the glenoid.

Still another embodiment of the invention is a system for coupling a graft to a bone that includes an offset measurement tool with a body, a pin with a cross-sectional center axis, the pin coupled to the body, wherein the pin is sized to fit within a hole in the graft, and two or more legs coupled to the body and extending to two or more different distances from the cross-sectional center axis of the pin. The system may also include a set of two or more offset drill guides. At least two of the drill guides may have at least a drill positioning opening, and an alignment surface having a spacing from a respective drill positioning opening. The two or more of the offset drill guides in the set of two or more offset drill guides include respective spacings that are coordinated with respective offsets that may be measured using respective legs that extend respective distances, the measuring legs being chosen from the two or more legs of the offset measurement tool.

An embodiment of the invention is a system for coupling a graft to a bone that includes an offset measurement tool with a body, a pin with a cross-sectional center axis, the pin coupled to the body, wherein the pin is sized to fit within a hole in the graft, and two or more legs coupled to the body and extending to two or more different distances from the cross-sectional center axis of the pin. The system may also include a means for guiding drilling of respective holes in a graft at a spacing coordinated with an offset that may be measured using a leg of the two or more legs of the offset measurement tool.

DETAILED DESCRIPTION

A system for coupling a graft to a bone is illustrated in FIGS. 1-8. The system is shown being used to perform a method embodiment in FIGS. 9-16. A graft 1 illustrated in FIGS. 2, 5, 6, 9-12, 15, and 16 is a severed portion of a coracoid process. In other embodiments, the graft may be any other natural or synthetic graft material that may be accepted in a patient's body. For example and without limitation, a graft may be an autograft from another portion of a patient's body, an allograft, a xenograft, a tricalcium phosphate graft, or a metal or polymer implant.

Figure 1:
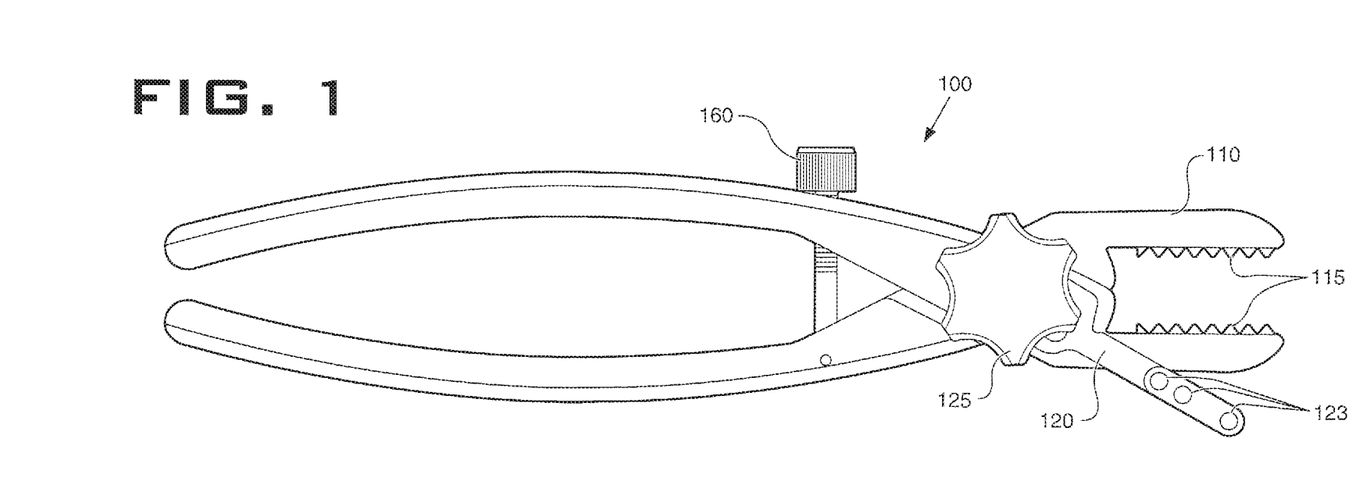
FIG. 1 is an elevation view of an embodiment of a graft preparation tool.
Figure 2:
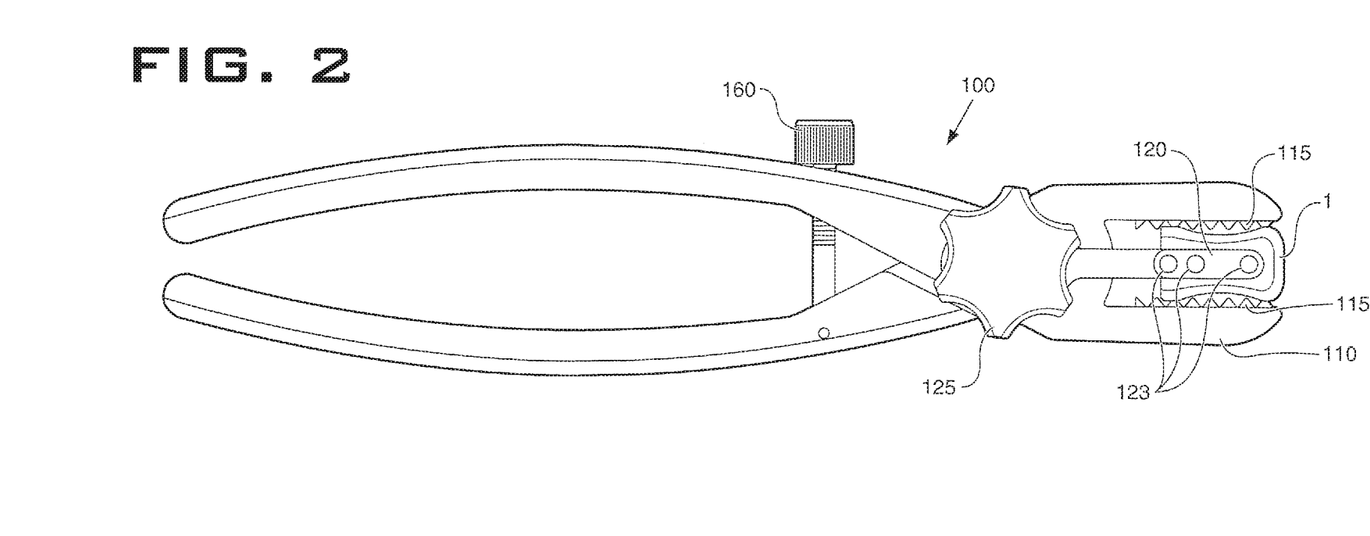
FIG. 2 is an elevation view of the graft preparation tool of FIG. 1 in which a graft is being held.
Figures 3, 4:
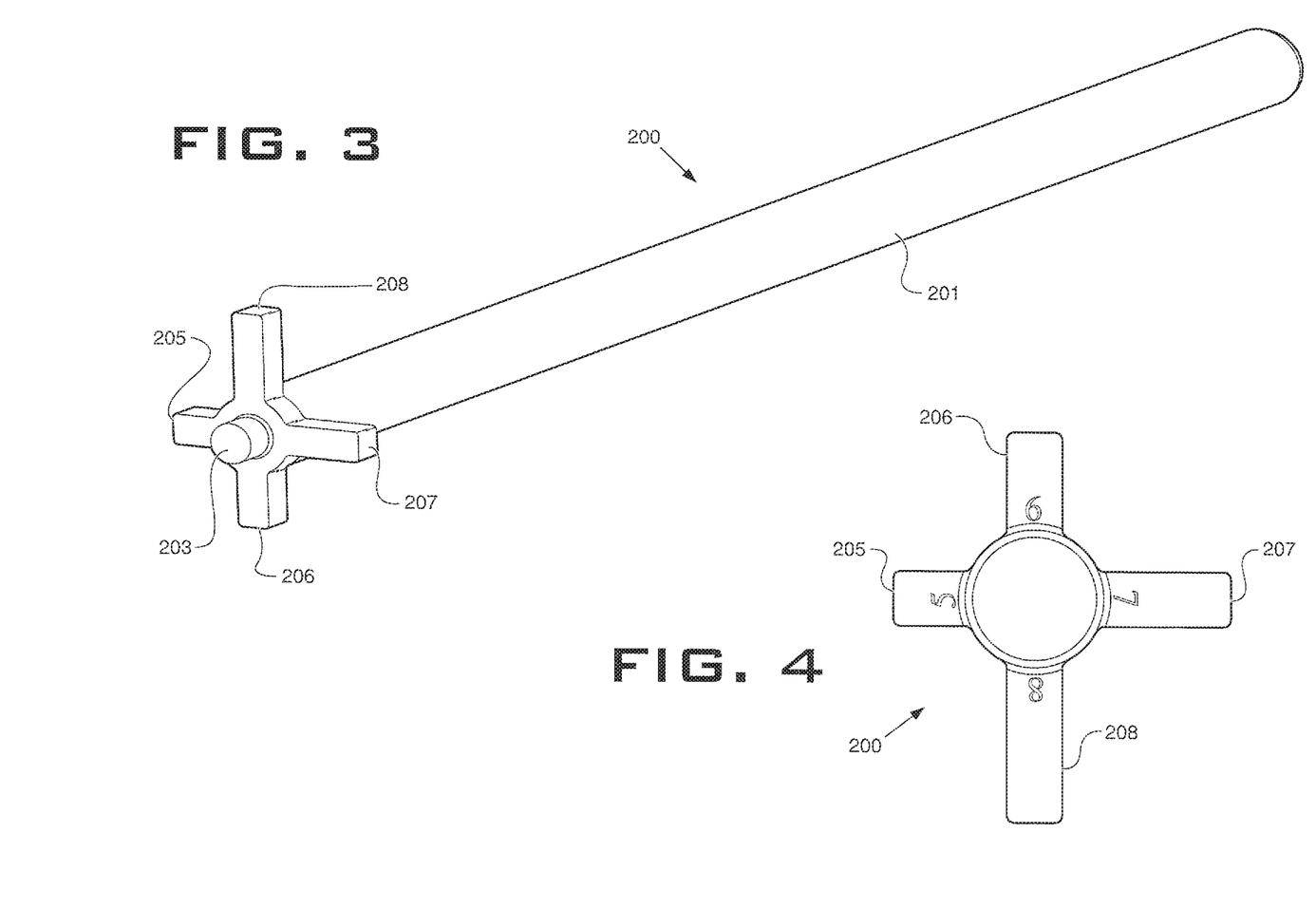
FIG. 3 is a perspective view of an embodiment of an offset measurement tool.
FIG. 4 is a proximal end elevation view of the offset measurement tool of FIG. 3.
Figures 5, 6:
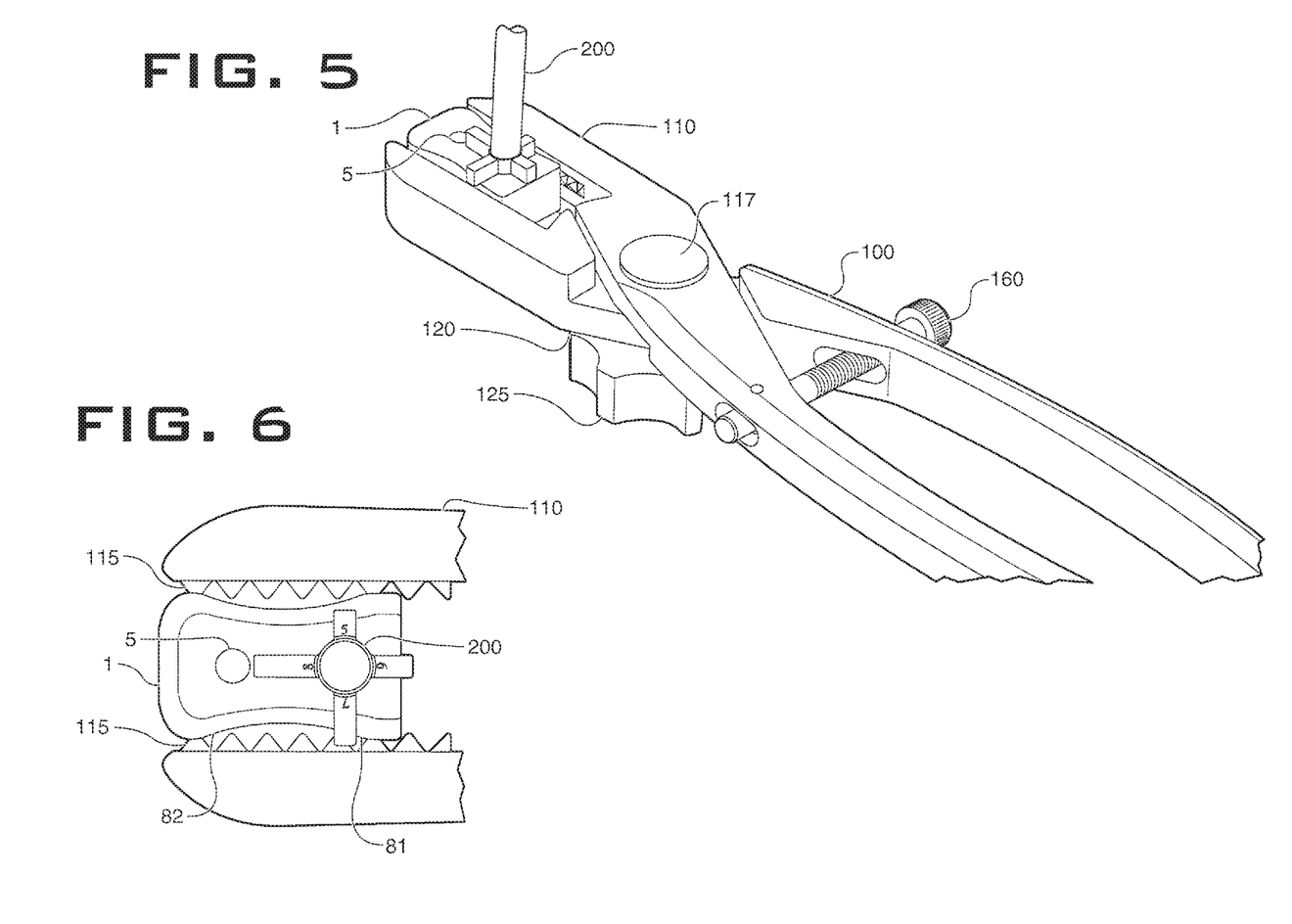
FIG. 5 is a perspective view of the offset measurement tool of FIG. 3 being used to measure a graft held in the graft preparation tool of FIG. 1.
FIG. 6 is an enlarged elevation view of the offset measurement tool in the same position on the graft held by the graft preparation tool as shown in FIG. 5.

A graft preparation tool 100 that includes a holder 110 and a drilling alignment mechanism 120 is shown in FIGS. 1, 2, 5, 6, and 11. The holder 110 depicted is configured to receive the graft 1 in textured jaws 115 that clamp the graft 1 in a position. In other embodiments, a holder may not clamp the graft, but may merely contain the graft while the graft is prepared. The holder 110 shown is a singly hinged plyer-type mechanism that brings the textured jaws 115 together about a single pivot pin 117 (FIG. 5). In other embodiments, a holder may include additional linkages that cause faces of jaws to move relative to one another in a parallel relationship so that grafts of various widths may be clamped between parallel faces of the jaws by a common instrument. A thread-driven vice may be used to clamp a graft within a holder of some embodiments. Any other mechanisms that effectively contain or clamp a graft for preparation may be used in other embodiments. Jaws of some embodiments are not necessarily textured or may include different types of texturing from the generally pyramid shapes shown. A locking bolt 160 is illustrated in FIGS. 1, 2, and 5 which may be used to lock the graft preparation tool 100 in a closed position. Other embodiments may include any type of effective locking mechanism.

Figure 11:
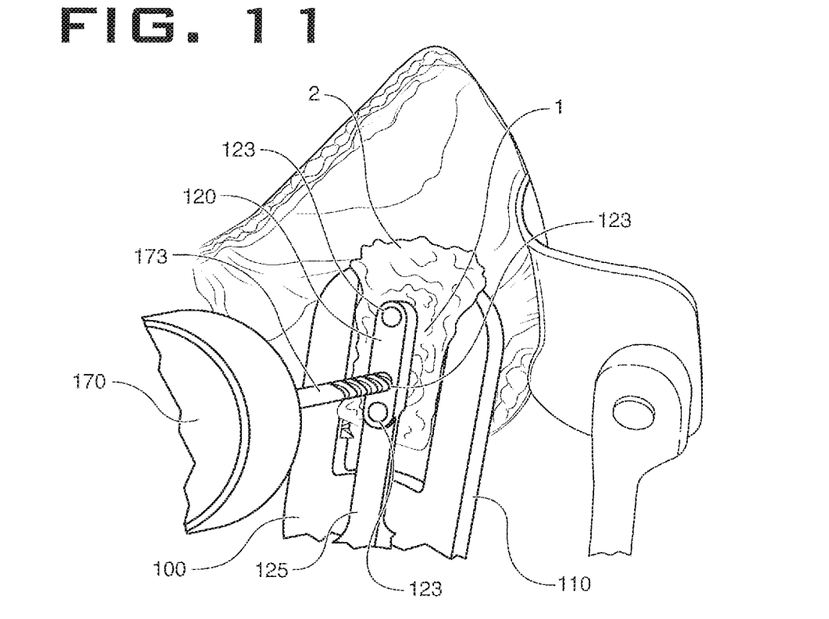
FIG. 11 is a perspective view of a patient's severed coracoid process being held in the graft preparation tool of FIG. 1 after being rotationally inverted approximately 180 degrees about a distal lateral axis of the severed coracoid process.

The drilling alignment mechanism 120 is configured to guide placement of one or more holes in the graft 1. The drilling alignment mechanism 120 shown includes three drill guiding holes 123 through which a drill bit 173 (FIG. 11) coupled with a drill 170 may be advanced to create one or more holes in the graft 1. The drill guiding holes 123 are configured to position placement of holes in the graft 1 by providing guides along respective axes of the drill guiding holes 123. With predetermined distance relationships among the three drill guiding holes 123, three differently spaced pairs of holes may be drilled through the drill guiding holes 123. For example, in the illustrated embodiment, the distance between the most distal and the center drill guiding holes 123 is 10 mm. Therefore, drilling through the center drill guide hole (FIG. 11) and the distal drill guiding hole will create substantially parallel holes in the graft 1 that are 10 mm apart. Other numbers of drill guiding holes or adjustable guide mechanisms may be used in other embodiments. Any other effective guiding or hole creation mechanism may be used in various embodiments. The drilling alignment mechanism 120 illustrated is movable relative to the holder 110. A knob 125 is configured to be tightened and loosened to restrict or permit movement of the drilling alignment mechanism 120 relative to the holder 110. As shown in FIG. 1, the drilling alignment mechanism 120 may be moved outside of the opening between the textured jaws 115 of the holder 110. Or as shown in FIGS. 2 and 11, the alignment mechanism 120 may be positioned between and adjacent to the opening between the textured jaw 115 when a graft 1 is being held in the holder 110 to guide drilling into the graft 1. Other types of relative adjustment between a holder and guiding mechanism may be used in other embodiments.

An offset measurement tool 200 is illustrated in FIGS. 3-6 and 12. The offset measurement tool 200 may be a part of a system for coupling a graft to a bone or may be a discrete instrument used to measure for placement of a graft or for other measurement purposes. The offset measurement tool 200, as shown specifically in FIGS. 3 and 4, includes a body 201, a pin 203 coupled to the body 201, and two or more legs 205, 206, 207, 208 coupled to the body 201. The body 201 illustrated is generally elongated cylindrical rod. However, other embodiments may include any effective shape or proportion to which a pin and legs may be coupled to accomplish measurement of an offset.

The pin 203 has a cross-sectional center axis that is aligned with a central longitudinal axis of the body 201. The pin 203 is sized to fit within at least one of the one or more holes in a graft. In particular for the illustrated embodiment, the pin 203 is sized to fit within any of the holes 5 drilled in the graft 1 through the drill guiding holes 123. A more distal hole 5 is visible in FIGS. 5 and 6, and a more proximal hole 5, having received the pin 203 of the offset measurement tool 200, is not visible in the illustrations. The pin 203 depicted has a circular cross-section. However, other embodiments may include any effective shape that would serve as a temporary fixation mechanism between a measurement tool and a graft. For example and without limitation, the cross-sectional shape of a pin of other embodiments may be square, triangular, rectangular, a higher number of sides polygon, star-shaped, or keyed to fit within a particularly configured hole created in a graft.

Legs 205, 206, 207, 208 illustrate a set of two or more legs coupled to the body 201 and extending to two or more distances from the cross-sectional center axis of the pin 203. The distances of the illustrated embodiment are lateral from and measured perpendicular to a central longitudinal axis through the cross-sectional center axis of the pin 203. In some embodiments, legs could be considered to be coupled to a pin rather than to a body, and to the extent that a cross-sectional center axis of the pin and a central longitudinal axis of a body are co-linear, distances measured laterally from and perpendicular to the longitudinal axis of the body and the cross-sectional center axis of the pin would be the same respective distances. The legs 205, 206, 207, 208 extend from the cross-sectional center axis of the pin 203 to the respective extents of the four legs about 5 mm, 6 mm, 7 mm, and 8 mm. The legs 205, 206, 207, 208 shown are each about 1 mm different distances from the cross-sectional center axis to their respective extents. Other embodiments may include any effective lengths of legs which may be at 1 mm intervals relative to one another or any other interval, and may includes uses of other units of measure. The legs 205, 206, 207, 208 depicted in FIGS. 4, 6, and 12 include numbers ("5", "6", "7", and "8") written on the legs 205, 206, 207, 208 that correspond with the distance from the cross-sectional center axis of the pin 203 to the extent of each of the legs on which the respective numbers are written. As illustrated, each of the numbers written is viewable from beyond a proximal end of the offset measurement tool 200. In other embodiments, some but not all numbers corresponding to length may be written on respective legs. In addition or in the alternative, colors, textures, or any other encoding or indicators may be used to designate respective lengths. In some embodiments, corresponding lengths may be included on proximal portions of an offset measurement tool such that a written length number may be associated with a rotational position of an offset measurement tool without viewing a number written directly on a leg.

The legs 205, 206, 207, 208 illustrated are each considered to extend substantially radially from the cross-sectional center axis of the pin 203. Each of the legs 205, 206, 207, 208 is substantially perpendicular to each leg adjacent to the leg. For example, the leg 207 is substantially perpendicular to legs 206 and 208, leg 208 is substantially perpendicular to legs 205 and 207, and so on. In other embodiments, there may be more or fewer legs coupled to a body and extending to distances from the cross-sectional center axis of a pin. For example and without limitation, there may be one, two, three, five, or more legs. Each of the legs may include a separate radially extending structure, as shown with the present embodiment, or what are considered to be legs may be interconnected portions of one or more shapes coupled to a body. The legs of other embodiments may be spaced radially equidistantly from one another, as are the leas 205, 206, 207, 208, or may include partially or thoroughly irregular spacing.

Figures 7, 8:
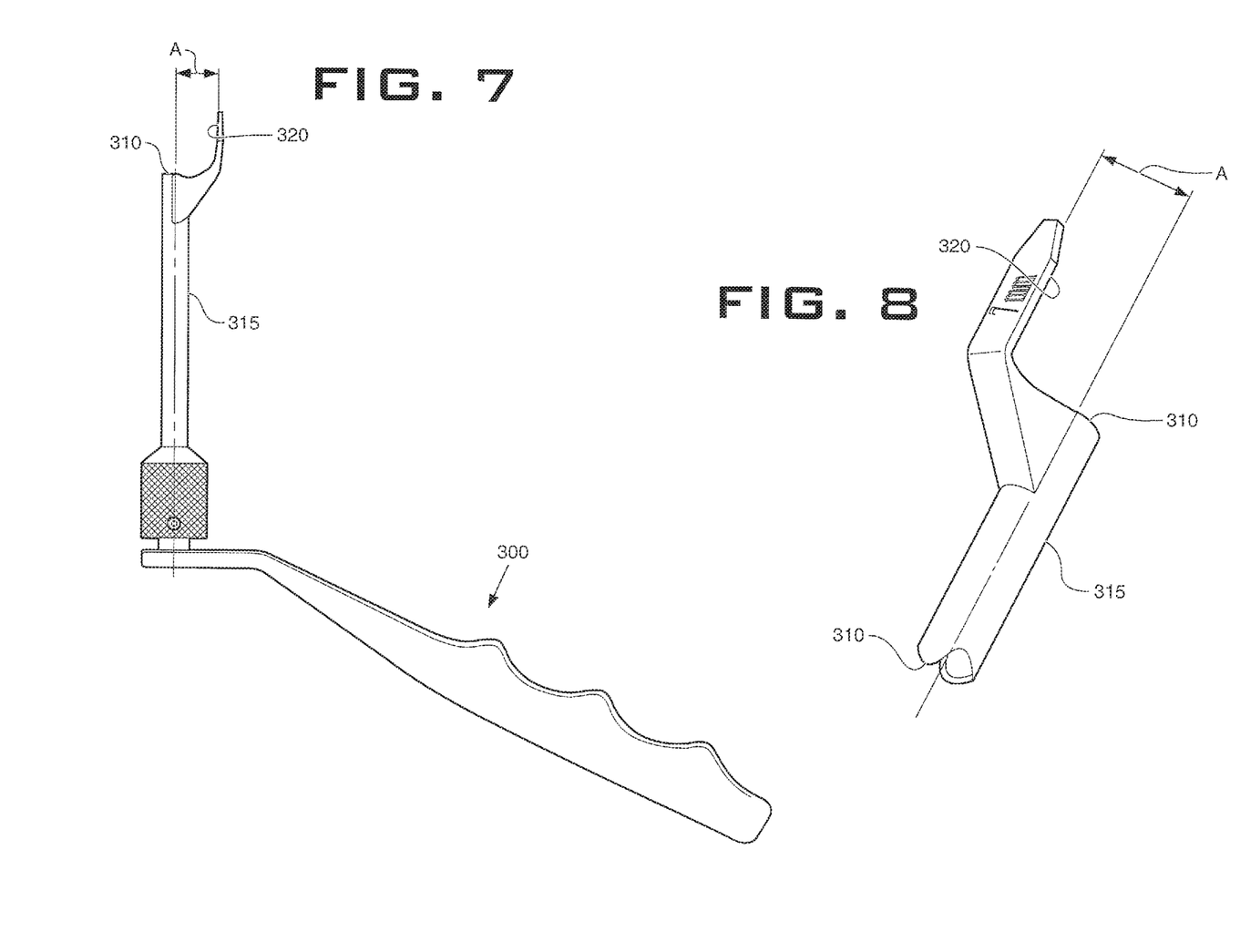
FIG. 7 is an elevation view of an embodiment of an offset drill guide.
FIG. 8 is an enlarged perspective view of a distal end of the offset drill guide illustrated in FIG. 7.
Figure 14:
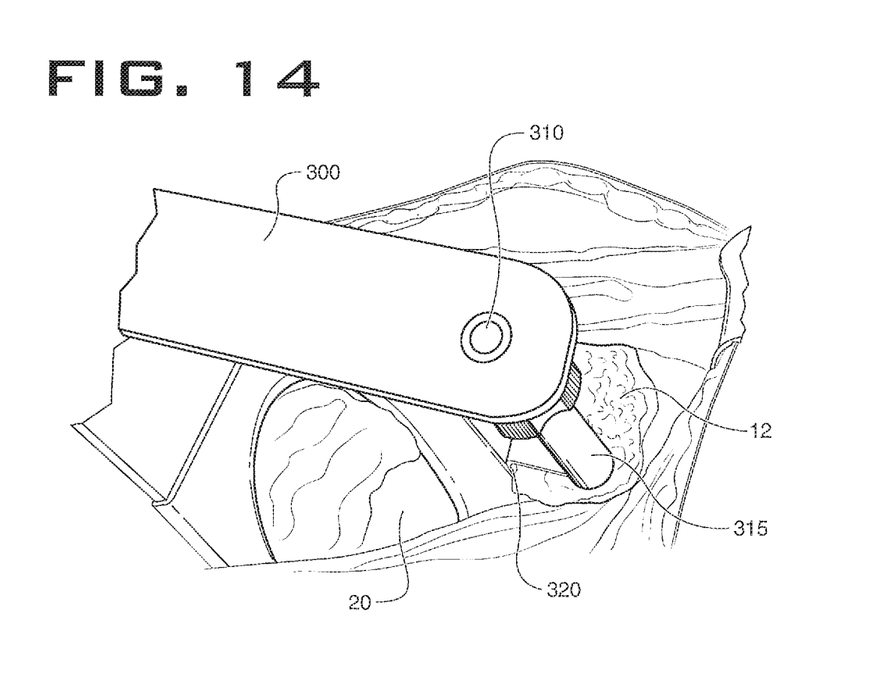
FIG. 14 is perspective view of the offset drill guide of FIG. 7 in position for a hole to be drilled in the prepared glenoid illustrated in FIG. 13.

Embodiments of the system for coupling a graft may also include an offset drill guide. An example offset drill guide 300 is illustrated in FIGS. 7, 8, and 14. The offset drill guide 300 shown includes a drill positioning opening 310 through a guide tube 315 and an alignment surface 320 set a distance from the drill positioning opening 310. In the embodiment shown, the set distance "A" is 7 mm from the alignment surface 320 to the central longitudinal axis or cross-sectional center of the drill positioning opening 310 and guide tube 315. In other embodiments where a drill positioning opening is not central to a guide tube central axis, the set distance may be measured between the alignment surface and the cross-sectional center of the drill positioning opening or similar location corresponding with where a hole will be created through an offset drill guide. The offset drill guide 300 is coordinated for use with the 7 mm offset measured with the offset measurement tool 200 in FIGS. 5, 6, and 12. Embodiments of the system for coupling a graft may include a set of offset drill guides that are coordinated with each of the potential offsets that may be measured with an offset measurement tool. One or more additional offset drill guides configured to be used to drill at distances estimated to be between or near a measured offset may also be included as part of a system. For example and without limitation, a 6.5 mm offset drill guide could be included for use when a measurement appears to be between 6 mm and 7 mm.

Figure 15:
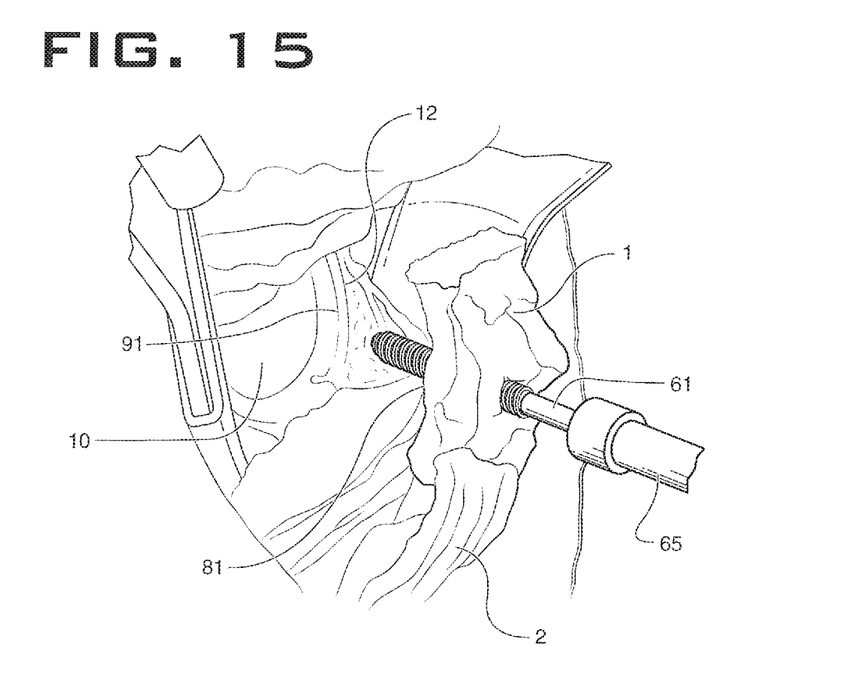
FIG. 15 is perspective view of a patient's severed coracoid process through which a first screw has been placed after being aligned with a hole drilled in the glenoid with the offset drill guide, as shown in FIG. 14.
Figure 16:
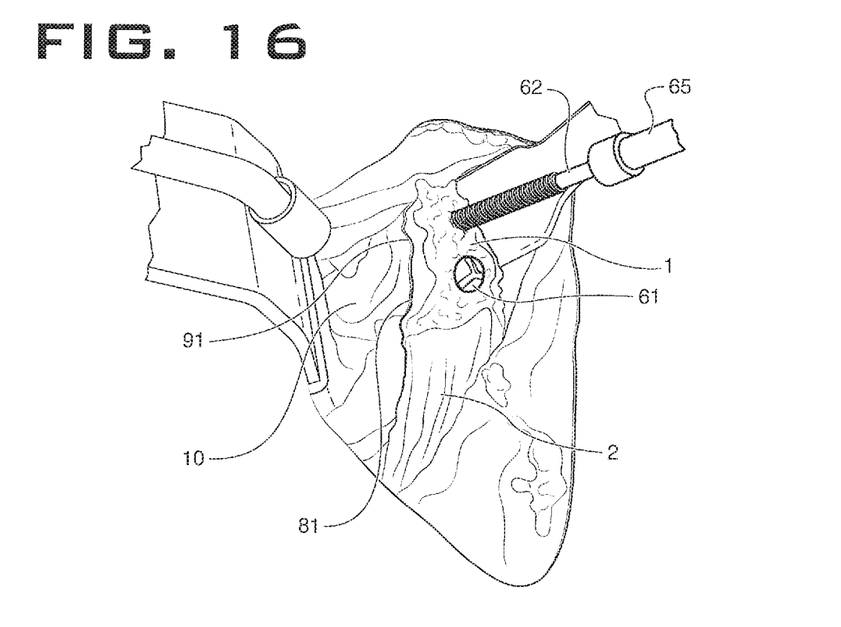
FIG. 16 is a perspective view of a second screw being place through a patient's coracoid process and into the patient's glenoid.

Some embodiments of the system for coupling a graft may also include in a kit, or may separately provide, the drill 170 and one or more drill bits. The example drill bit 173 is shown coupled to the drill 170 in FIG. 11. Different size drill bits and different styles of drills may be used in some embodiments. A drill may be a rotary power drill as depicted in the example of the drill 170 or may be any other effective tool, however powered or driven, capable of assisting with the creation of a hole. Likewise, a drill bit or similar device of other embodiments may be any type of mechanism useful in creation of a hole. Some embodiments of the system for coupling a graft may also include a guide pin that may be used to define a path between a hole in a graft and a hole in a bone to which the graft is to be connected for the purpose of alignment. A guide pin may also be used in combination with a cannulated fastener sized to fit over the guide pin and be directed by the guide pin to a desired implantation location through one or both of the graft and the bone to which the graft is to be connected. An example first screw 61 is shown in FIGS. 15 and 16 along with a driver 65. An example second screw 62 is depicted in FIG. 16. These or any other effective fastener and driver or inserter may be used in other embodiments.

An embodiment of the invention may include a kit that contains two or more of a graft preparation tool, an offset measurement tool, an offset drill guide, a drill, a drill bit, a screw, a driver, and a guide pin. A kit may include two or more of each of these components, each in the same size or in a variety of sizes as may promote efficient performance of graft alignment surgical procedures.

Figure 9:
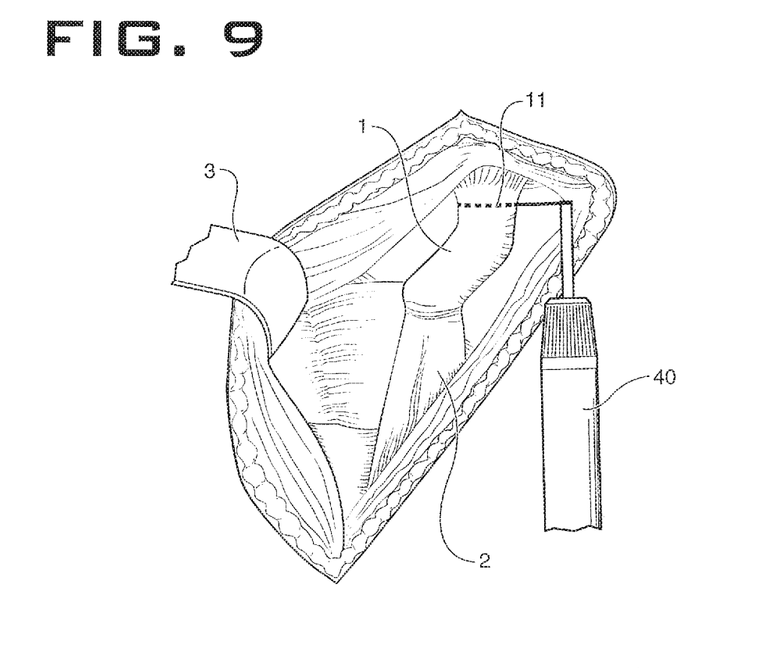
FIG. 9 is a perspective view of a partially exposed portion of a patient's right shoulder, including illustrations of a retractor and a bone saw.
Figure 10:
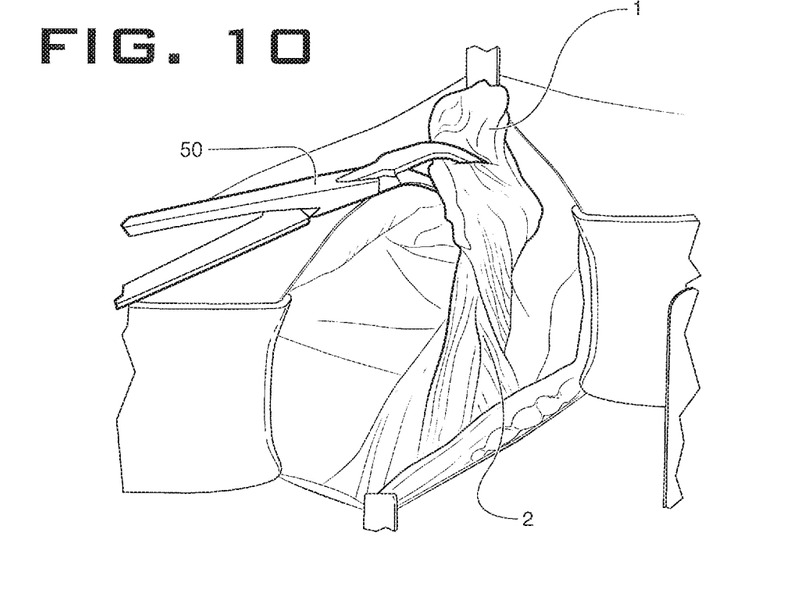
FIG. 10 is a perspective view of a patient's severed coracoid process being held in a position where it has been rotationally inverted approximately 180 degrees about its generally longitudinal axis.

A depiction of a method embodiment of the invention is illustrated in FIGS. 9-16. The particular method illustrated is a Latarjet protocol procedure. However, similar graft preparation, anatomical preparation, graft to bone alignment, and graft to bone coupling may be accomplished at other locations and for other purposes. A perspective view of a partially exposed portion of a patient's right shoulder is shown in FIG. 9. A retractor 3 and a bone saw 40 are also shown in FIG. 9. Retractors of any effective type may be used and retractors of other sizes and types are shown in appropriate use herein without further explanation. The bone saw 40 is shown with an end-cutting blade aligned to cut a coracoid process or graft 1 along a projection line 11. In the illustrated method, a conjoined tendon 2 near a distal end of the graft 1 is left intact. Method embodiments include severing at least a portion of the severed coracoid process from a patient. The graft 1 of the illustrated embodiment may be referred to throughout either as the graft 1 or as the severed coracoid process. Cutting of a coracoid process may be accomplished with the bone saw 40 or by use of any other effective device or method. A patient's severed coracoid process is shown being held in a position with a clamp 50 where the severed coracoid process has been rotationally inverted approximately 180 degrees about its generally longitudinal axis in FIG. 10.

An act of some embodiments is the drilling of one or more holes through the graft 1. In some embodiments, soft tissues are removed from the graft 1 at least on a side that is to be coupled to bone. Holes for fasteners may be created in or through the graft 1. In FIG. 11, the severed coracoid process is shown being held in the graft preparation tool 100 that includes the holder 110 and the drilling alignment mechanism 120 that is coupled to the holder 110. As described in detail herein, the drilling alignment mechanism 120 is adjustably coupled to the holder 110 and includes the drill guiding holes 123 to direct drilling of the holes 5 (FIGS. 5 and 6) through the graft 1. The drilling of a hole 5 in the graft 1 is being shown in FIG. 11 with the drill bit 173 being rotated by the drill 170. In the illustrated embodiment, the graft 1 is held in the graft preparation tool 100 after being rotationally inverted approximately 180 degrees about a distal lateral axis of the graft 1. Drilling or creating of holes through a severed coracoid process or another graft of other embodiments is not necessarily accomplished with the use of the graft preparation tool 100, but in some circumstances may be.

Figure 12:
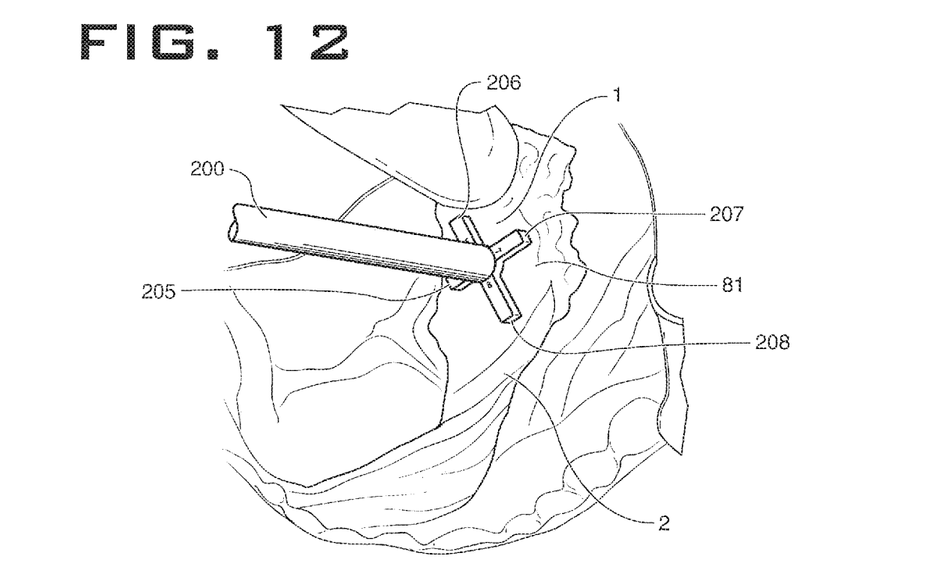
FIG. 12 is a perspective view of a patient's severed coracoid process being measured by the offset measurement tool of FIG. 3 after being rotationally inverted approximately 180 degrees about its generally longitudinal axis.

As shown in FIG. 12, the offset measurement tool 200 may be provided for use in determining an offset distance from a hole in the severed coracoid process to an edge 81 of the severed coracoid process. The offset measurement tool provided may be the same as the offset measurement tool 200 or similar devices described in detail herein. Some embodiments may include the use of an alternative offset measurement tool. The graft 1 is shown being measured in FIG. 12 by the offset measurement tool 200 after being rotationally inverted approximately 180 degrees about its generally longitudinal axis. Method embodiments may also include the act of measuring an offset distance from a first hole 5 in the graft 1 to the edge 81 (FIGS. 6, 12, 15, and 16) of the graft 1 that is to be aligned with a face 91 of a glenoid 10 by inserting the pin 203 (FIG. 3) of the offset measurement tool 200 into the first one of the holes 5 in the graft 1 and observing which extent of one of the two or more legs 205, 206, 207, 208 most nearly aligns with the edge 81 of the graft 1 that is to be aligned with the face 91 of the glenoid 10. As can be seen in FIG. 12, the leg 207 most nearly aligns with the edge 81 of the graft 1 that is to be aligned with the face 91 of the glenoid 10. In some embodiments, such an observation occurs when an offset measurement tool is rotated about the axis of the hole in the graft in which the offset measurement tool is inserted. For example, the offset measurement tool 200 is rotated in the more distal hole 5 while an observation regarding alignment of an extent of a leg 205, 206, 207, 208 relative to the edge 81 of the graft 1 is made. By observation, it is noted that the leg 207, with an offset distance of 7 mm, most nearly aligns with the edge 81 of the graft 1 that is to be aligned with the face 91 of the glenoid 10. In the illustrated embodiment the act of measuring an offset distance includes observing a number written on the leg in this case the number "7" on the leg 207. As shown, the leg 207 most nearly aligns with the edge 81 of the graft 1 that is to be aligned with the face 91 of the glenoid 10. In other embodiments, whichever number or other indicator associated with the extent of whichever leg most nearly aligns with the edge 81 of the graft 1 that is to be aligned with the face 91 of the glenoid 10 would similarly be noted. In the disclosed embodiment, the number is viewable from beyond a proximal end of the offset measurement tool 200. In this or other embodiments such a number or another indicator may also be viewable through a tube, a retractor, an endoscope, or other viewing device. In some embodiments, numbers or other indicators may be included on proximal portions of an offset measurement tool such that the numbers or indicators may be associated with a rotational position of an offset measurement tool without viewing a number written directly on a leg or at a distal end of an offset measurement tool.

Figure 13:
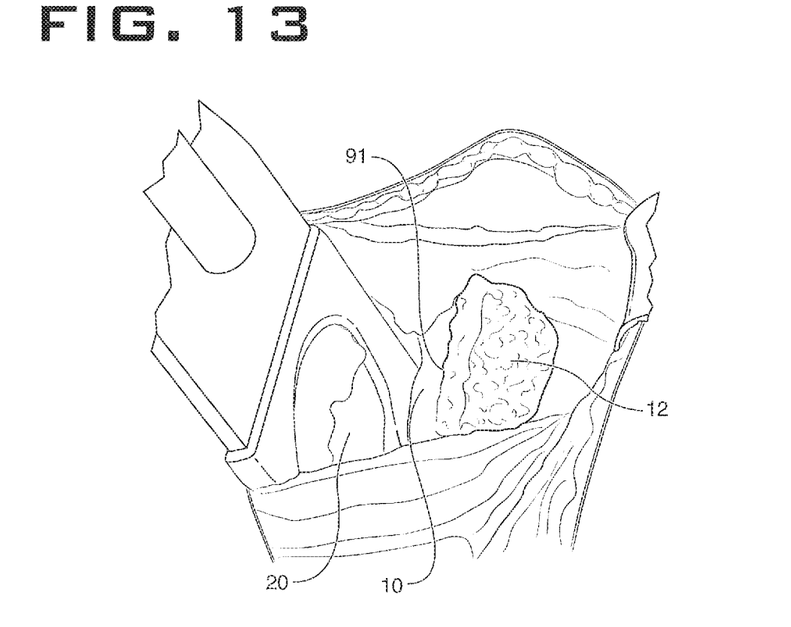
FIG. 13 is perspective view illustrating preparation of a surface of a patient's glenoid to which a graft is to be coupled.

Some method embodiments include preparing a bone to receive a graft. A prepared glenoid surface 12 of the glenoid 10 to which a graft may be coupled is shown in FIG. 13. An articular proximal surface of a humerus 20 is also illustrated in FIGS. 13 and 14. In the embodiment shown, soft tissues and an outer portion of the glenoid 10 have been removed to expose bleeding bone and to expose an edge along the face 91 of the glenoid 10.

An act of some method embodiments also includes selecting an offset drill guide that correlates with the offset distance measured from one of the holes 5 in the graft 1 to an edge 81 of the graft 1 with the offset measurement tool 200. The offset drill guide 300 shown in FIGS. 7, 8, and 14 includes a 7 mm offset distance and was selected for use in the current embodiment because of correlation with the 7 mm offset measured with the offset measurement tool 200, as shown in FIGS. 6 and 12. As shown in FIG. 14 the offset drill guide 300 may be aligned with the face of the glenoid 10, and a first hole may be drilled into the prepared glenoid surface 12. More specifically in the illustrated embodiment, the alignment surface 320 (FIGS. 7, 8, and 14) is aligned with the face of the glenoid 10. This positioning properly sets the distance from the face of the glenoid 10 and then a surgeon may place the offset drill guide 300 along a line generally parallel with the face of the glenoid 10 prior to drilling through the offset drill guide 300.

Method embodiments may also include aligning one of the holes in the graft 1 with one of the holes created in the glenoid 10. For example, the more distal hole 5 in the graft 1 may be aligned with the hole created in the glenoid 10 shown being set for drilling in FIG. 14. Alignment may be accomplished with the assistance of a guide wire that is extended through both the more distal hole 5 and the hole created in the glenoid 10. The graft 1 may then be held in the aligned position while the first screw 61 (FIGS. 15 and 16) is inserted. In another embodiment, the first screw 61 may be partially advanced through a hole in the graft 1, as shown in FIG. 15, and the first screw 61 itself may be used to align the more distal hole 5 with the hole created in the glenoid 10. Other embodiments may include any other effective mechanism or means of alignment and screw placement. The first screw 61 may then be advanced to couple the graft 1 to the glenoid 10. In the embodiment shown, the driver 65 is used to rotate and advance the first screw 61. The first screw 61 may be the only fastener used in some embodiments. The first screw 61 may be fully advanced prior to any subsequent screws being implanted or may be partially advanced to allow for continued adjustment of the graft 1 relative to the glenoid 10 during the procedure.

The second screw 62 is shown being inserted through the graft 1 and into the glenoid 10 in FIG. 16. There at least two ways of drilling for and inserting the second screw 62. One way of placing the second screw 62 includes aligning the edge 81 of the graft 1 with the face 91 of the glenoid 10 and drilling a second hole in the prepared glenoid surface 12 (FIGS. 13-15) of the glenoid 10 through a second one of the holes in the graft 1. For example, with the graft 1 in the position shown in FIG. 16, a second hole in the glenoid 10 may be drilled through the more proximal hole 5 (FIG. 6) in the graft 1 prior to a inserting the second screw 62 through the graft 1 and into the second hole in the glenoid 10.

Another way of placing the second screw 62 includes using the offset measurement tool 200 to preplan the placement of the second screw 62 based on measurements taken prior to inserting the first screw 61 through the graft 1. This method may include measuring an offset distance from a second one of the holes 5 in the graft 1 to an edge 82 (FIG. 6) of the graft 1 that is to be aligned with a face 91 of a glenoid 10. This measurement may be accomplished by inserting the pin 203 of the offset measurement tool 200 into the second one of the holes 5 in the graft 1 and observing which extent of one of the two or more legs 205, 206, 207, 208 most nearly aligns with the edge 82 of the graft 1 that is to be aligned with the face 91 of the glenoid 10 when the offset measurement tool 200 is rotated about the axis of the second one of the holes 5 in the graft 1. This method embodiment may also include selecting an offset drill guide, such as the offset drill guide 300, that correlates with the offset distance measured from the second one of the holes 5 in the graft 1 to an edge 82 of the graft 1 by measuring with the offset measurement tool 200. The offset drill guide 300 may then be aligned with the face 91 of the glenoid 10 at an appropriate linear distance away from the first one of the holes 5 in the graft 1. The appropriate linear distance may be established with a linkage configured for insertion in the first one of the holes 5 and rotatable coupling with the appropriate offset drill guide. A second hole may then be drilled in the glenoid 10 through the offset drill guide with the appropriate amount of offset. Such a method embodiment may subsequently include aligning the second one of the holes 5 in the graft 1 with the second hole in the glenoid 10, and inserting the second screw 62 through the second one of the holes 5 in the graft 1 and through the second hole in the glenoid 10 to couple the graft 1 to the glenoid 10.

Various embodiments of a system wholly or its components individually may be made from any biocompatible material. For example and without limitation, biocompatible materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as distal, proximal, over, near, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A system for coupling a graft to a bone comprising:
an offset measurement tool comprising:
a body having a proximal end, a distal end, and a longitudinal axis extending between the proximal and distal ends,
a pin with a cross-sectional center axis extending along the longitudinal axis of the body, the pin coupled to the distal end of the body, wherein the pin is sized to fit within a hole in the graft, and
two or more legs coupled to the body between the distal end of the body and the pin and extending to two or more different distances from the cross-sectional center axis of the pin; and
a set of two or more offset drill guides, at least two of the drill guides comprising:
a drill positioning opening, and
an alignment surface having a spacing from a respective drill positioning opening,
wherein two or more of the offset drill guides in the set of two or more offset drill guides include respective spacings that are coordinated with respective offsets that may be measured using respective legs that extend respective distances, the measuring legs being chosen from the two or more legs of the offset measurement tool.

2. The system of claim 1, wherein the pin has a circular cross-section.

3. The system of claim 1, wherein the two or more legs extend radially from the cross-sectional center axis of the pin.

4. The system of claim 1, wherein the two or more legs coupled to the body are four legs coupled to the body.

5. The system of claim 4, wherein each of the four legs extends radially from the cross-sectional center axis of the pin and each of the four legs is perpendicular to an adjacent leg.

6. The system of claim 4, wherein the respective distances from the cross-sectional center axis of the pin to the respective extents of the four legs are about 5 mm, 6 mm, 7 mm, and 8 mm.

7. The system of claim 1, wherein the two or more different distances from the cross-sectional center axis are each about 1 mm different from one or more of the other distances.

8. The system of claim 1, further comprising one or more numbers written on one or more of the two or more legs that correspond with the distance from the cross-sectional center axis of the pin to an extent of the leg on which the number is written.

9. The system of claim 8, wherein the one or more numbers are viewable from beyond the proximal end of the body of the offset measurement tool.

10. The system of claim 1, further comprising a drill and a drill bit.

11. The system of claim 1, further comprising a graft preparation tool comprising:
   a holder in which the graft may be positioned, and
   a drilling alignment mechanism configured to guide placement of one or more holes in the graft.

12. The system of claim 11, wherein the holder is a clamp.

13. The system of claim 11, wherein the drilling alignment mechanism is movable relative to the holder.

14. The system of claim 11, wherein the drilling alignment mechanism includes two or more holes in a predetermined relationship to one another and wherein the two or more holes are configured to position placement of holes in the graft by providing guides for drilling along respective axes of the two or more holes.

15. A system for coupling a graft to a bone comprising:
   a graft preparation tool comprising:
      a holder in which the graft may be positioned, and
      a drilling alignment mechanism configured to guide placement of one or more holes in the graft;
   an offset measurement tool comprising:
      a body having a proximal end, a distal end, and a longitudinal axis extending between the proximal and distal ends,
      a pin with a cross-sectional center axis extending along the longitudinal axis of the body, the pin coupled to the distal end of the body, wherein the pin is sized to fit within at least one of the one or more holes in the graft, and
      two or more legs coupled to the body between the distal end of the body and the pin and extending to two or more different distances from the cross-sectional center axis of the pin; and
   an offset drill guide comprising:
      a drill positioning opening, and
      an alignment surface set a distance from the drill positioning opening,
   wherein the distance set from the drill positioning opening is coordinated with an offset measured with the offset measurement tool.

* * * * *